US011889856B2

(12) United States Patent
St. Charles

(10) Patent No.: US 11,889,856 B2
(45) Date of Patent: *Feb. 6, 2024

(54) ORAL FOAM COMPOSITION

(71) Applicant: NICOVENTURES TRADING LIMITED, London (GB)

(72) Inventor: Frank Kelley St. Charles, Bowling Green, KY (US)

(73) Assignee: Nicoventures Trading Limited, London (GB)

(*) Notice: Subject to any disclaimer, the term of this patent is extended or adjusted under 35 U.S.C. 154(b) by 358 days.

This patent is subject to a terminal disclaimer.

(21) Appl. No.: 16/706,968

(22) Filed: Dec. 9, 2019

(65) Prior Publication Data
US 2021/0169122 A1 Jun. 10, 2021

(51) Int. Cl.
A24B 13/00 (2006.01)
A24B 15/42 (2006.01)
A24B 15/30 (2006.01)

(52) U.S. Cl.
CPC ............ A24B 13/00 (2013.01); A24B 15/303 (2013.01); A24B 15/42 (2013.01)

(58) Field of Classification Search
None
See application file for complete search history.

(56) References Cited

U.S. PATENT DOCUMENTS

| | | | |
|---|---|---|---|
| 4,374,155 A | 2/1983 | Igoe et al. | |
| 5,159,942 A * | 11/1992 | Brinkley | A24B 15/12 131/297 |
| 5,417,229 A | 5/1995 | Summers et al. | |
| 6,138,683 A | 10/2000 | Hersh et al. | |
| 6,344,222 B1 * | 2/2002 | Cherukuri | A61K 9/0058 424/440 |
| 6,845,777 B2 | 1/2005 | Pera | |
| 6,958,143 B2 | 10/2005 | Choi et al. | |
| 7,032,601 B2 | 4/2006 | Atchley et al. | |
| 7,056,541 B1 | 6/2006 | Stahl et al. | |
| 7,507,427 B2 | 3/2009 | Andersen et al. | |
| 7,810,507 B2 | 10/2010 | Dube et al. | |
| 7,833,555 B2 | 11/2010 | Andersen et al. | |
| 7,861,728 B2 | 1/2011 | Holton, Jr. et al. | |
| 7,900,637 B2 | 3/2011 | Fagerstrom et al. | |
| 7,950,399 B2 | 5/2011 | Winterson et al. | |
| 8,069,861 B2 | 12/2011 | Sinclair | |
| 8,124,147 B2 | 2/2012 | Cheng et al. | |
| 8,293,295 B2 | 10/2012 | Andersen et al. | |
| 8,336,557 B2 | 12/2012 | Kumar et al. | |
| 8,343,532 B2 | 1/2013 | Dam et al. | |
| 8,424,541 B2 | 4/2013 | Crawford et al. | |
| 8,469,036 B2 | 6/2013 | Williams et al. | |
| 8,469,037 B2 | 6/2013 | Liu et al. | |
| 8,529,875 B2 | 9/2013 | Andersen | |
| 8,529,914 B2 | 9/2013 | Fuisz et al. | |
| 8,545,870 B2 | 10/2013 | Dupinay et al. | |
| 8,591,967 B2 | 11/2013 | Andersen et al. | |
| 8,613,285 B2 | 12/2013 | Fuisz | |
| 8,627,828 B2 | 1/2014 | Strickland et al. | |
| 8,642,016 B2 | 2/2014 | Chau et al. | |
| 8,714,163 B2 | 5/2014 | Kumar et al. | |
| 8,741,348 B2 | 6/2014 | Hansson et al. | |
| 8,747,562 B2 | 6/2014 | Mishra et al. | |
| 8,828,361 B2 | 9/2014 | Anderson | |
| 8,833,378 B2 | 9/2014 | Axelsson et al. | |
| 8,846,075 B2 | 9/2014 | Johnson et al. | |
| 8,858,984 B2 | 10/2014 | Dam et al. | |
| 8,863,755 B2 | 10/2014 | Zhuang et al. | |
| 8,871,243 B2 | 10/2014 | Fankhauser et al. | |
| 8,931,493 B2 | 1/2015 | Sebastian et al. | |
| 8,945,593 B2 | 2/2015 | LoCoco et al. | |
| 8,978,661 B2 | 3/2015 | Atchley et al. | |
| 8,992,974 B2 | 3/2015 | McCarty | |
| 9,027,567 B2 | 5/2015 | Gee et al. | |
| 9,039,839 B2 | 5/2015 | Beeson et al. | |
| 9,044,035 B2 | 6/2015 | Jackson et al. | |

(Continued)

FOREIGN PATENT DOCUMENTS

| | | |
|---|---|---|
| CN | 103005680 | 4/2013 |
| CN | 103263507 | 8/2013 |
| CN | 103494324 | 1/2014 |
| CN | 105192876 | 12/2015 |
| CN | 105595404 | 5/2016 |
| WO | WO 2018/224546 | 12/2018 |
| WO | WO 2019/036243 | 2/2019 |

OTHER PUBLICATIONS

Robichaud Meagan et al., "Tobacco companies introduce 'tobacco free' nicotine pouches", Tob Control 2019, Nov. 21, 2019, 1-2, National Library of Medicine, doi: 10.1136/tobaccocontrol-2019-055321.

Belščak-Cvitanović et al., "Improving the Controlled Delivery Formulations of Caffeine in Alginate Hydrogel Beads Combined with Pectin, Carrageenan, Chitosan and Psyllium," Food Chemistry, vol. 167, pp. 378-386, Year: 2015.

Primary Examiner — Dennis R Cordray

(74) Attorney, Agent, or Firm — Womble Bond Dickinson (US) LLP

(57) ABSTRACT

The disclosure provides a foam composition including a cellulosic foam stabilizer, a sweetener, optionally a natural gum, water, and a flavoring agent or an active ingredient or both a flavoring agent and an active ingredient. The disclosure also provides a method of forming a foam composition, including mixing an aqueous slurry of a cellulosic foam stabilizer with a sweetener, an optional natural gum, an optional alkali metal salt, and a flavoring agent or an active ingredient or both a flavoring agent and an active ingredient to form a mixture; introducing air into the mixture through stirring or bubbling to form a foam; dividing the foam into a plurality of discrete portions; and optionally drying the discrete portions of foam.

10 Claims, No Drawings

(56) References Cited

U.S. PATENT DOCUMENTS

| | | |
|---|---|---|
| 9,084,439 B2 | 7/2015 | Holton, Jr. |
| 9,155,321 B2 | 10/2015 | Cantrell et al. |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,204,667 B2 | 12/2015 | Cantrell et al. |
| 9,237,768 B2 | 1/2016 | Carroll et al. |
| 9,358,296 B2 | 6/2016 | McCarty |
| 9,372,033 B2 | 6/2016 | Lampe et al. |
| 9,386,800 B2 | 7/2016 | Sebastian et al. |
| 9,402,414 B2 | 8/2016 | Griscik et al. |
| 9,402,809 B2 | 8/2016 | Axelsson et al. |
| 9,414,624 B2 | 8/2016 | Carroll et al. |
| 9,420,825 B2 | 8/2016 | Beeson et al. |
| 9,468,233 B2 | 10/2016 | Macko et al. |
| 9,474,303 B2 | 10/2016 | Holton, Jr. |
| 9,521,864 B2 | 12/2016 | Gao et al. |
| 9,565,867 B2 | 2/2017 | Wittorff et al. |
| 9,629,392 B2 | 4/2017 | Holton, Jr. |
| 9,675,102 B2 | 6/2017 | Hunt et al. |
| 9,763,928 B2 | 9/2017 | Duggins et al. |
| 9,775,376 B2 | 10/2017 | Cantrell et al. |
| 9,801,409 B1 | 10/2017 | Smith |
| 9,848,634 B2 | 12/2017 | Fuisz |
| 9,854,830 B2 | 1/2018 | Gao et al. |
| 9,884,015 B2 | 2/2018 | Gao et al. |
| 9,907,748 B2 | 3/2018 | Borschke et al. |
| 9,925,145 B2 | 3/2018 | Hubinette et al. |
| 9,930,909 B2 | 4/2018 | Gao et al. |
| 9,999,243 B2 | 6/2018 | Gao et al. |
| 10,039,309 B2 | 8/2018 | Carroll et al. |
| 10,045,976 B2 | 8/2018 | Fusco et al. |
| 10,092,715 B2 | 10/2018 | Axelsson et al. |
| 10,130,120 B2 | 11/2018 | Mishra et al. |
| 10,143,230 B2 | 12/2018 | Mishra et al. |
| 10,149,850 B2 | 12/2018 | Mishra et al. |
| 10,172,810 B2 | 1/2019 | McCarty |
| 10,244,786 B2 | 4/2019 | Gao et al. |
| 10,334,873 B2 | 7/2019 | Mishra et al. |
| 10,357,054 B2 | 7/2019 | Marshall et al. |
| 10,375,984 B2 | 8/2019 | Hernandez Garcia et al. |
| 10,426,726 B2 | 10/2019 | Neergaard |
| 10,463,070 B2 | 11/2019 | Carroll et al. |
| 10,532,046 B2 | 1/2020 | Rogers et al. |
| 10,543,205 B2 | 1/2020 | Wittorff et al. |
| 2004/0118422 A1 | 6/2004 | Lundin et al. |
| 2004/0131752 A1 | 7/2004 | Best et al. |
| 2006/0191548 A1* | 8/2006 | Strickland ............. A24B 13/02 131/347 |
| 2007/0031539 A1 | 2/2007 | Calton |
| 2008/0081071 A1 | 4/2008 | Sanghvi et al. |
| 2008/0166395 A1 | 7/2008 | Roush |
| 2009/0023819 A1 | 1/2009 | Axelsson |
| 2009/0065013 A1 | 3/2009 | Essen et al. |
| 2009/0133703 A1 | 5/2009 | Strickland et al. |
| 2009/0253754 A1 | 10/2009 | Selmin et al. |
| 2009/0293895 A1 | 12/2009 | Axelsson et al. |
| 2009/0301504 A1 | 12/2009 | Worthen et al. |
| 2010/0004294 A1 | 1/2010 | Axelsson et al. |
| 2010/0061940 A1 | 3/2010 | Axelsson et al. |
| 2010/0187143 A1 | 7/2010 | Essen et al. |
| 2010/0260690 A1 | 10/2010 | Kristensen et al. |
| 2010/0294292 A1 | 11/2010 | Hodin et al. |
| 2010/0330247 A1 | 12/2010 | Montaigne et al. |
| 2011/0139164 A1 | 6/2011 | Mua et al. |
| 2011/0220130 A1 | 9/2011 | Mua et al. |
| 2011/0250150 A1* | 10/2011 | Pedersen ............. A61K 9/0058 424/48 |
| 2011/0268809 A1 | 11/2011 | Brinkley et al. |
| 2012/0031415 A1 | 2/2012 | Essen et al. |
| 2012/0037175 A1 | 2/2012 | Cantrell et al. |
| 2012/0039981 A1 | 2/2012 | Pedersen et al. |
| 2012/0263659 A1* | 10/2012 | Subkowski ........... C07D 495/22 544/298 |
| 2013/0078307 A1 | 3/2013 | Holton, Jr. et al. |
| 2013/0118512 A1 | 5/2013 | Jackson et al. |
| 2013/0152953 A1 | 6/2013 | Mua et al. |
| 2013/0177646 A1 | 7/2013 | Hugerth et al. |
| 2013/0206150 A1 | 8/2013 | Duggins et al. |
| 2013/0251779 A1 | 9/2013 | Svandal et al. |
| 2013/0340773 A1 | 12/2013 | Sebastian et al. |
| 2014/0130813 A1 | 5/2014 | Strehle |
| 2014/0154301 A1 | 6/2014 | Chau et al. |
| 2014/0255452 A1 | 9/2014 | Reddick et al. |
| 2015/0068544 A1 | 3/2015 | Moldoveanu et al. |
| 2015/0068545 A1 | 3/2015 | Moldoveanu et al. |
| 2015/0071972 A1 | 3/2015 | Holton, Jr. et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0296868 A1 | 10/2015 | Sutton |
| 2016/0000140 A1 | 1/2016 | Sebastian et al. |
| 2016/0073676 A1 | 3/2016 | Cantrell et al. |
| 2016/0073689 A1 | 3/2016 | Sebastian et al. |
| 2016/0157515 A1 | 6/2016 | Chapman et al. |
| 2016/0192703 A1 | 7/2016 | Sebastian et al. |
| 2016/0279071 A1* | 9/2016 | Park ................... A61K 9/7007 |
| 2017/0007594 A1 | 1/2017 | Borschke |
| 2017/0164651 A1 | 6/2017 | Mua et al. |
| 2017/0165252 A1 | 6/2017 | Mua et al. |
| 2017/0172995 A1 | 6/2017 | Repaka et al. |
| 2017/0280764 A1 | 10/2017 | Sahlen et al. |
| 2017/0312261 A1 | 11/2017 | Changoer et al. |
| 2017/0318858 A1 | 11/2017 | Hodin et al. |
| 2018/0140007 A1 | 5/2018 | Aspgren et al. |
| 2018/0140521 A1 | 5/2018 | Geonnotti et al. |
| 2018/0140554 A1 | 5/2018 | Wittorff |
| 2018/0153211 A1 | 6/2018 | Persson |
| 2018/0235273 A1 | 8/2018 | Carroll et al. |
| 2018/0255826 A1 | 9/2018 | Persson et al. |
| 2018/0257801 A1 | 9/2018 | Persson |
| 2019/0037909 A1 | 2/2019 | Greenbaum et al. |
| 2019/0255035 A1 | 8/2019 | Bruun |
| 2020/0037638 A1 | 2/2020 | Faraci et al. |
| 2020/0128870 A1 | 4/2020 | Hassler et al. |
| 2020/0138706 A1 | 5/2020 | Rudraraju et al. |
| 2020/0275689 A1 | 9/2020 | Lewerenz |
| 2020/0297026 A1 | 9/2020 | Kannisto et al. |
| 2020/0305496 A1 | 10/2020 | Gessesse |

\* cited by examiner

ORAL FOAM COMPOSITION

FIELD OF THE DISCLOSURE

The present disclosure relates to products intended for human use. The products are configured for oral use and deliver substances such as flavors and/or active ingredients during use. Such products may include tobacco or a component derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

BRIEF SUMMARY

The present disclosure generally provides compositions configured for oral use. The compositions are intended to impart a taste when used orally, and typically also deliver one or more active ingredients to the consumer, such as nicotine. The compositions are in the form of a foam, and in certain embodiments, are adapted for introduction into the oral cavity.

The disclosure includes, without limitations, the following embodiments. Where an embodiment refers to a composition as further including one or more components selected from a list, such a reference includes compositions that include a single member from a single classification of components from the list (e.g., a single sweetener), or two or more members from a single classification of components from the list (e.g., two sweeteners), or combinations of one or more members from each of two or more classifications of components from the list (e.g., a sweetener and an alkali metal salt).

Embodiment 1: A foam composition, comprising a cellulosic foam stabilizer (e.g., hydroxypropylmethylcellulose), a sweetener (e.g., one or more sugar alcohols and/or maltodextrin), optionally a natural gum (e.g., xanthan gum), water, and a flavoring agent or an active ingredient or both a flavoring agent and an active ingredient.

Embodiment 2: The foam composition of Embodiment 1, wherein the cellulosic foam stabilizer is a cellulose ether.

Embodiment 3: The foam composition of any one of Embodiments 1 to 2, wherein the cellulose ether is selected from the group consisting of methylcellulose, hydroxypropylcellulose, hydroxypropylmethylcellulose, hydroxyethyl cellulose, carboxymethylcellulose, and combinations thereof.

Embodiment 4: The foam composition of any one of Embodiments 1 to 3, wherein the sweetener is selected from the group consisting of sugar alcohols, maltodextrin, sucralose, and combinations thereof.

Embodiment 5: The foam composition of any one of Embodiments 1 to 4, wherein the sweetener comprises isomalt and maltodextrin.

Embodiment 6: The foam composition of any one of Embodiments 1 to 5, wherein the natural gum is selected from the group consisting of xanthan gum, guar gum, gum arabic, ghatti gum, gum tragacanth, karaya gum, locust bean gum, gellan gum, and combinations thereof.

Embodiment 7: The foam composition of any one of Embodiments 1 to 6, further comprising one or more salts (e.g., alkali metal salts).

Embodiment 8: The foam composition of any one of Embodiments 1 to 7, wherein the one or more salts are alkali metal salts selected from the group consisting of sodium chloride, sodium carbonate, sodium bicarbonate, and combinations thereof.

Embodiment 9: The foam composition of any one of Embodiments 1 to 8, comprising an aqueous tobacco extract (optionally spray-dried or freeze-dried).

Embodiment 10: The foam composition of any one of Embodiments 1 to 9, wherein the active ingredient is selected from the group consisting of a nicotine component, botanicals, nutraceuticals, stimulants, amino acids, vitamins, cannabinoids, and combinations thereof.

Embodiment 11: The foam composition of any one of Embodiments 1 to 10, comprising from about 0.001 to about 10% by weight of a nicotine component (e.g., from about 0.01% to about 10% by weight of the composition or about 0.5% to about 5%), calculated as the free base and based on the total weight of the composition.

Embodiment 12: The foam composition of any one of Embodiments 1 to 11, wherein the composition is substantially free of tobacco material, excluding any nicotine component present.

Embodiment 13: The foam composition of any one of Embodiments 1 to 12, comprising:
- about 2 to about 80% by weight water (e.g., about 10 to about 20% or about 70 to about 80% or about 10 to about 80%);
- about 5 to about 75% by weight of cellulosic foam stabilizer (e.g., about 5 to about 15% or about 50 to about 70%);
- about 5 to about 30% by weight of sweetener (e.g., about 8 to about 25%);
- about 0.1 to about 5% by weight of natural gum (e.g., about 0.1 to about 1.0% or about 0.2 to about 0.6%);
- optionally, about 0.1 to about 5% by weight of one or more alkali metal salts (e.g., about 0.1 to about 2% or about 0.5 to about 1.5%); and
- about 0.001 to about 10% by weight of one or more active ingredients, flavoring agents, or combinations thereof (e.g., from about 0.01% to about 10% by weight of the composition or about 0.5% to about 5%).

Embodiment 14: The foam composition of any one of Embodiments 1 to 13, wherein the foam composition is non-crosslinked.

Embodiment 15: A method of forming a foam composition, comprising:
- mixing an aqueous slurry of a cellulosic foam stabilizer with a sweetener, an optional natural gum, an optional alkali metal salt, and a flavoring agent or an active ingredient or both a flavoring agent and an active ingredient to form a mixture;
- introducing air into the mixture through stirring or bubbling to form a foam;
- dividing the foam into a plurality of discrete portions; and
- optionally drying the discrete portions of foam.

Embodiment 16: The method of Embodiment 15, wherein the mixing comprises forming an aqueous solution comprising one or more dissolvable components selected from alkali metal salts, flavoring agents, and active ingredients; mixing a solid mixture comprising a sweetener and a natural gum into the aqueous solution; and mixing the aqueous slurry of a cellulosic foam stabilizer into the aqueous solution, wherein the mixing of the solid mixture and the mixing of the aqueous slurry can occur in any order.

Embodiment 17: The method of any one of Embodiments 15 to 16, wherein the mixing comprises mixing one or more dissolvable components selected from alkali metal salts, flavoring agents, and active ingredients with the aqueous slurry of a cellulosic foam stabilizer to form a first mixture; and mixing a solid mixture comprising a sweetener and a natural gum into the first mixture.

Embodiment 18: The method of any one of Embodiments 15 to 17, wherein the foam is formed without crosslinking.

Embodiment 19: The method of any one of Embodiments 15 to 18, wherein the cellulosic foam stabilizer is a cellulose ether.

Embodiment 20: The method of any one of Embodiments 15 to 19, wherein the cellulose ether is selected from the group consisting of methylcellulose, hydroxypropylcellulose, hydroxypropylmethylcellulose, hydroxyethyl cellulose, carboxymethylcellulose, and Embodiment 21: Use of a cellulosic foam stabilizer, optionally in combination with a natural gum, to stabilize a foam composition comprising a flavoring agent or an active ingredient or both a flavoring agent and an active ingredient, particularly a foam composition according to any one of Embodiments 1 to 14.

These and other features, aspects, and advantages of the disclosure will be apparent from a reading of the following detailed description. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

The present disclosure relates to foam compositions, which are typically adapted for oral use, and which utilize a cellulosic foam stabilizer, optionally in combination with a natural gum, to stabilize the foam composition. Such compositions also include a flavoring agent or an active ingredient or both a flavoring agent and an active ingredient. As used herein, a foam composition is a composition with entrapped bubbles or pockets of gas, typically air. Although not bound by a theory of operation, the use of a cellulosic foam stabilizer in such compositions is believed to provide suitable stabilization of the foam without the need to use crosslinked components, which can add complexity to the composition and its method of manufacture. As used herein, reference to non-crosslinked means the composition does not include any reactive components/ingredients that form covalent crosslinks during mixing/manufacture of the foam composition. The example individual components of the composition are described herein below.

Cellulosic Foam Stabilizer

The cellulosic foam stabilizer is typically a cellulose derivative or a combination of such derivatives. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). Example cellulose ethers are available under the tradenames BENECEL™ and METHOCEL™.

In some embodiments, the composition comprises from about 5 to about 75% of the cellulose derivative by weight, based on the total weight of the composition, with certain embodiments comprising about 5 to about 15% or about 50 to about 70%, by weight of cellulose derivative. Use of higher concentrations of the cellulosic foam stabilizer can lead to increases in certain physical properties of the foam, such as increased stiffness or resilience of the foam. In one embodiment, the cellulose derivative is HPMC.

Water

The water content of the composition, prior to use by a consumer of the product, may vary according to the desired properties. In certain embodiments, the water content is relatively high (e.g., water is the predominant ingredient). In other embodiments, water is present in lower amounts, such as in embodiments characterized by larger amounts of cellulosic foam stabilizer. For example, compositions of the invention can include about 2 to about 80% by weight water (e.g., about 10 to about 20% or about 70 to about 80%).

Flavoring Agent

As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, *Eucalyptus*, lavender, cardamon, nutmeg, cinnamon, clove, cascarilla, sandalwood, honey, jasmine, ginger, anise, sage, licorice, lemon, orange, apple, peach, lime, cherry, strawberry, and any combinations thereof. See also, Leffingwell et al., Tobacco Flavoring for Smoking Products, R. J. Reynolds Tobacco Company (1972), which is incorporated herein by reference. Flavorings also may include components that are considered moistening, cooling or smoothening agents, such as *Eucalyptus*. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The flavoring agent generally comprises at least one volatile flavor component. As used herein, "volatile" refers to a chemical substance that forms a vapor readily at ambient temperatures (i.e., a chemical substance that has a high vapor pressure at a given temperature relative to a nonvolatile substance). Typically, a volatile flavor component has a molecular weight below about 400 Da, and often include at least one carbon-carbon double bond, carbon-oxygen double bond, or both. In one embodiment, the at least one volatile flavor component comprises one or more alcohols, aldehydes, aromatic hydrocarbons, ketones, esters, terpenes, terpenoids, or a combination thereof. Non-limiting examples of aldehydes include vanillin, ethyl vanillin, p-anisaldehyde, hexanal, furfural, isovaleraldehyde, cuminaldehyde, benzaldehyde, and citronellal. Non-limiting examples of ketones include 1-hydroxy-2-propanone and 2-hydroxy-3-methyl-2-cyclopentenone-1-one. Non-limiting examples of esters include allyl hexanoate, ethyl heptanoate, ethyl hexanoate, isoamyl acetate, and 3-methylbutyl acetate. Non-limiting examples of terpenes include sabinene, limonene, gamma-terpinene, beta-farnesene, nerolidol, thujone, myrcene, geraniol, nerol, citronellol, linalool, and eucalyptol. In one embodiment, the at least one volatile flavor component comprises one or more of ethyl vanillin, cinnamaldehyde, sabinene, limonene, gamma-terpinene, beta-farnesene, or citral. In one embodiment, the at least one volatile flavor component comprises ethyl vanillin.

The amount of flavoring agent utilized in the composition can vary, but is typically up to about 10 weight percent, and certain embodiments are characterized by a flavoring agent content of at least about 0.1 weight percent, such as about 0.5 to about 10 weight percent, about 1 to about 6 weight percent, or about 2 to about 5 weight percent, based on the total weight of the composition.

Active Ingredient

The composition may additionally include one or more active ingredients including, but not limited to, a nicotine component, botanical ingredients (e.g., lavender, peppermint, chamomile, basil, rosemary, ginger, cannabis, ginseng, maca, hemp, eucalyptus, rooibos, fennel, citrus, cloves, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C, and/or cannabinoids, such as tetrahydrocannabinol (THC) and cannabidiol (CBD)). The particular percentages and choice of ingredients will vary depending upon the desired flavor, texture, and other characteristics. Example active ingredients would include any ingredient known to impact one or more biological functions within the body, such as ingredients that furnish pharmacological activity or other direct effect in the diagnosis, cure, mitigation, treatment, or prevention of disease, or which affect the structure or any function of the body of humans or other animals (e.g., provide a stimulating action on the central nervous system, have an energizing effect, an antipyretic or analgesic action, or an otherwise useful effect on the body).

In certain embodiments, a nicotine component may be included in the composition. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, nicotine is in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride. In some embodiments, the nicotine component or a portion thereof is a nicotine salt with at least a portion of the one or more organic acids as disclosed herein above.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the composition, such as in a range from about 0.001% to about 10%. In some embodiments, the nicotine component is present in a concentration from about 0.1% w/w to about 10% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about from about 0.1% w/w to about 2.5%, from about 0.1% to about 2.0%, from about 0.1% to about 1.5%, or from about 0.1% to about 1% by weight, calculated as the free base and based on the total weight of the composition. These ranges can also apply to other active ingredients noted herein.

Sweeteners

The composition typically further comprises one or more sweeteners. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, stevia, honey, and the like. Examples of artificial sweeteners include sucralose, isomaltulose, maltodextrin, saccharin, aspartame, acesulfame K, neotame and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). When present, a representative amount of sweetener may make up from about 0.1 to about 30 percent or more of the of the composition by weight, for example, from about 5 to about 28%, from about 10 to about 26%, from about 15 to about 25%, or from about 20 to about 25% of the composition on a weight basis, based on the total weight of the composition. In certain embodiments, the sweetener (or combination of sweeteners) is present in an amount of about 5 to about 30% by weight (e.g., about 8 to about 25%);

Salts

In some embodiments, the composition may further comprise a salt (e.g., alkali metal salts), typically employed in an amount sufficient to provide desired sensory attributes to the composition. Non-limiting examples of suitable salts include sodium chloride, potassium chloride, ammonium chloride, flour salt, and the like. The salts may also include alkali metal buffers such as metal carbonates (e.g., potassium carbonate or sodium carbonate), or metal bicarbonates such as sodium bicarbonate, and the like.

When present, a representative amount of salt is about 0.1 percent by weight or more, about 1.0 percent by weight or more, or at about 1.5 percent by weight or more, but will typically make up about 10 percent or less of the total weight of the composition, or about 7.5 percent or less or about 5 percent or less (e.g., about 0.5 to about 5 percent by weight). In certain embodiments, the composition includes about 0.1 to about 5% by weight of one or more alkali metal salts (e.g., about 0.1 to about 2% or about 0.5 to about 1.5%).

Natural Gum

In certain embodiments, the composition includes a gum, for example, a natural gum. As used herein, a natural gum refers to polysaccharide materials of natural origin that have binding properties, and which are also useful as a thickening or gelling agents. Such gums are also useful for enhancing stability of a foam. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the composition.

Humectants

In certain embodiments, one or more humectants may be employed in the composition. Examples of humectants include, but are not limited to, glycerin, propylene glycol, and the like. Humectants can impact mouthfeel and other organoleptic properties of the composition, and will also impact water activity of the composition.

When present, a humectant will typically make up about 25% or less of the weight of the composition (e.g., from about 0.5 to about 20% by weight). When present, a representative amount of humectant is about 0.1% to about 20% by weight, or about 10% to about 15% by weight, based on the total weight of the composition.

Binding Agents

An additional binder component may be employed in certain embodiments, in amounts sufficient to provide the desired physical attributes and organoleptic properties to the composition. Binding agents typically also function as viscosity modifiers. Typical binders can be organic or inorganic, or a combination thereof. Representative binders include povidone, sodium alginate, starch-based binders, pectin, carrageenan, pullulan, zein, and the like, and combinations thereof. The amount of binder utilized in the composition can vary, but is typically up to about 30 weight percent, and certain embodiments are characterized by a binder content of at least about 0.1% by weight, such as about 1 to about 30% by weight, or about 5 to about 10% by weight, based on the total weight of the composition.

Filler Component

Certain embodiments of the compositions described herein may also include at least one filler component. Such fillers may fulfill multiple functions, such as enhancing certain organoleptic properties like texture and mouthfeel. Generally, the fillers are porous particulate materials and are cellulose-based. For example, suitable particulate fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential particulate fillers include dextrose, calcium carbonate, calcium phosphate, and lactose. Combinations of fillers can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the composition based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, starch sodium octenyl succinate.

In some embodiments, the particulate filler is a cellulose material or cellulose derivative. One particularly suitable particulate filler for use in the products described herein is microcrystalline cellulose ("mcc"). The mcc may be synthetic or semi-synthetic, or it may be obtained entirely from natural celluloses. The mcc may be selected from the group consisting of AVICEL grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. In one embodiment, the composition comprises mcc as the particulate filler component. The quantity of mcc present in the composition as described herein may vary according to the desired properties.

The amount of filler can vary, but is typically up to about 30 percent of the composition by weight, based on the total weight of the composition. A typical range of particulate filler (e.g., mcc) within the composition can be from about 0.1 to about 25 percent by total weight of the composition, for example, from about 1.0, about 1.5, about 2.0, about 2.5, or about 3.0, to about 10, about 15, about 20, or about 25 weight percent.

Organic Acid

As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids (—$CO_2H$) or sulfonic acids (—$SO_2OH$). As used herein, reference to organic acid means an organic acid that is intentionally added. In this regard, an organic acid may be intentionally added as a specific composition ingredient as opposed to merely being inherently present as a component of another composition ingredient (e.g., the small amount of organic acid which may inherently be present in a composition ingredient such as a tobacco material). In some embodiments, the one or more organic acids are added neat (i.e., in their free acid, native solid or liquid form) or as a solution in, e.g., water. In some embodiments, the one or more organic acids are added in the form of a salt, as described herein below.

In some embodiments, the organic acid is an alkyl carboxylic acid. Non-limiting examples of alkyl carboxylic acids include formic acid, acetic acid, propionic acid, octanoic acid, nonanoic acid, decanoic acid, undecanoic acid, dodecanoic acid, stearic acid, oleic acid, linoleic acid, linolenic acid, and the like. In some embodiments, the organic acid is an alkyl sulfonic acid. Non-limiting examples of alkyl sulfonic acids include propanesulfonic acid and octanesulfonic acid.

In some embodiments, the organic acid is citric acid, malic acid, tartaric acid, octanoic acid, benzoic acid, a toluic acid, salicylic acid, or a combination thereof. In some embodiments, the organic acid is benzoic acid. In some embodiments, the organic acid is citric acid.

In alternative embodiments, a portion, or even all, of the organic acid may be added in the form of a salt with an alkaline component, which may include, but is not limited to, nicotine. Non-limiting examples of suitable salts, e.g., for nicotine, include formate, acetate, propionate, isobutyrate, butyrate, alpha-methylbutyate, isovalerate, beta-methylvalerate, caproate, 2-furoate, phenylacetate, heptanoate, octanoate, nonanoate, oxalate, malonate, glycolate, benzoate, tartrate, levulinate, ascorbate, fumarate, citrate, malate, lactate, aspartate, salicylate, tosylate, succinate, pyruvate, and the like. In some embodiments, the organic acid or a portion thereof may be added in the form of a salt with an alkali metal such as sodium, potassium, and the like. In organic acids having more than one acidic group (such as a di- or tri-carboxylic acid), in some instances, one or more of these acid groups may be in the form of such a salt. Suitable non-limiting examples include monosodium citrate, disodium citrate, and the like. In some embodiments, the organic acid is a salt of citric acid, malic acid, tartaric acid, octanoic acid, benzoic acid, a toluic acid, salicylic acid, or a combination thereof. In some embodiments, the organic acid is a mono or di-ester of a di- or tri-carboxylic acid, respectively, such as a monomethyl ester of citric acid, malic acid, or tartaric acid, or a dimethyl ester of citric acid.

The amount of organic acid present in the composition may vary. Generally, the composition comprises from about 0.1 to about 10% by weight of organic acid, present as one or more organic acids, based on the total weight of the composition. In some embodiments, the composition comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% organic acid by weight, based on the total weight of the composition. In some embodiments, the composition comprises from about 0.1 to about 0.5% by weight of organic acid, for example, about 0.1, about 0.15, about 0.2, about 0.25, about 0.3, about 0.35, about 0.4, about 0.45, or about 0.5% by weight, based on the total weight of the composition. In some embodiments, the composition comprises from about 0.25 to about 0.35% by weight of organic acid, for example, from about 0.25, about 0.26, about 0.27, about 0.28, about 0.29, or about 0.3, to about 0.31, about 0.32, about 0.33, about 0.34, or about 0.35% by weight, based on the total weight of the composition. In the case where a salt of an organic acid is added, the percent by weight is calculated based on the weight of the free acid, not including any counter-ion which may be present.

The quantity of acid present will vary based on the acidity and basicity of other components which may be present in the composition (e.g., nicotine, salts, buffers, and the like). Accordingly, in certain embodiment, the organic acid is provided in a quantity sufficient to provide a pH of 7.0 or below, (typically about 6.8 or below, about 6.6 or below, or about 6.5 or below) of the composition. In certain embodiments the acid inclusion is sufficient to provide a composition pH of from about 4.0 to about 7.0; for example, from about 4.5, about 5.0, about 5.5, or about 6.0, to about 6.5, or about 7.0. In some embodiments, the organic acid is provided in a quantity sufficient to provide a pH of the composition of from about 5.5 to about 6.5, for example, from about 5.5, about 5.6, about 5.7, about 5.8, about 5.9, or about 6.0, to about 6.1, about 6.2, about 6.3, about 6.4, or about 6.5.

Buffering Agents

In certain embodiments, the composition of the present disclosure can comprise additional pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. The amounts of buffering agent utilized can vary, depending in part on the presence (and amount) of pH-modifying components in the composition, such as organic acids, nicotine salts, and the like. Where present, the buffering agent is typically present in an amount less than about 5 percent based on the weight of the composition, for example, from about 0.5% to about 5%, such as, e.g., from about 0.75% to about 4%, from about 0.75% to about 3%, or about 0.5% to about 1.5%, or from about 1% to about 2% by weight, based on the total weight of the composition. Non-limiting examples of suitable buffers include alkali metals acetates, glycinates, phosphates, glycerophosphates, citrates, carbonates, hydrogen carbonates, borates, certain amino acids (e.g., glycine or glycylglycine), or mixtures thereof Colorants A colorant may be employed in amounts sufficient to provide the desired physical attributes to the composition. Examples of colorants include various dyes and pigments, such as caramel coloring and titanium dioxide. The amount of colorant utilized in the composition can vary, but when present is typically up to about 3 weight percent, such as from about 0.1%, about 0.5%, or about 1%, to about 3% by weight, based on the total weight of the composition.

Tobacco Material

In some embodiments, the composition may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N.* x *sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

Various parts or portions of the plant of the *Nicotiana* species can be included within a composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material is used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like.

For the preparation of oral products, it is typical for a harvested plant of the *Nicotiana* species to be subjected to a curing process. The tobacco materials incorporated within the composition for inclusion within products as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

Tobacco materials can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent (e.g., an aqueous solvent) that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein. Tobacco extracts can be utilized in a spray-dried or freeze-dried form.

Typical inclusion ranges for tobacco materials can vary depending on the nature and type of the tobacco material, and the intended effect on the final composition, with an example range of up to about 60% by weight (or up to about 50% by weight or up to about 40% by weight or up to about 30% by weight), based on total weight of the composition (e.g., about 0.1 to about 50% by weight). In some embodiments, the products of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or 0% by weight of tobacco material.

Other Additives

Other additives can be included in the disclosed composition. For example, the composition can be processed, blended, formulated, combined and/or mixed with other materials or ingredients. The additives can be artificial, or can be obtained or derived from herbal or biological sources. Examples of further types of additives include thickening or gelling agents (e.g., fish gelatin), emulsifiers, oral care additives (e.g., thyme oil, *Eucalyptus* oil, and zinc), preservatives (e.g., potassium sorbate and the like), or combinations thereof. Other examples include plant-based oils, such as olive oil, almond oil, avocado seed oil, coconut oil, corn oil, cottonseed oil, flax seed oil, grapeseed oil, hemp oil, palm kernel oil, peanut oil, pumpkin seed oil, rice bran oil, safflower seed oil, sesame seed oil, sunflower seed oil, soybean oil, or walnut oil.

See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final composition, with an example range of up to about 10% by weight, based on total weight of the composition (e.g., about 0.1 to about 5% by weight or about 0.5% to about 1.5%).

The aforementioned additives can be employed together (e.g., as additive formulations) or separately (e.g., individual additive components can be added at different stages involved in the preparation of the final composition). Furthermore, the aforementioned types of additives may be encapsulated as provided in the final product or composition. Exemplary encapsulated additives are described, for example, in WO2010/132444 to Atchley, which has been previously incorporated by reference herein.

In some embodiments, one or more components of the composition (e.g., a filler or a tobacco material) can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, any particulate material referenced herein (e.g., filler component or tobacco material) can be characterized as having at least 50% by weight of particles with a particle size as measured by sieve analysis of no greater than about 1000 μm, such as no greater than about 500 μm, such as no greater than about 400 μm, such as no greater than about 350 μm, such as no greater than about 300 μm. In some embodiments, at least 60% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 70% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 80% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 90% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 95% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300

μm. In some embodiments, at least 99% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, approximately 100% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm.

In certain embodiments, even smaller particle sizes could be used, particularly if the product is intended to be ingested. For example, in some embodiments, any of the particle size ranges noted previously could include ranges such as no greater than about 100 μm, no greater than about 50 μm, or no greater than about 30 μm.

Preparation of the Composition

The foam compositions of the invention are prepared, for example, by providing an initial amount of water in a mixing vessel and adding the remaining components of the composition to the mixing vessel with continuous or intermittent stirring or agitation. The remaining components of the composition can be added together or individually over multiple addition steps. Mixing typically occurs at room temperature. The process will include introduction of air (or other gas) into the composition in order to form entrapped pockets of gas that define the foam structure. The method is typically practiced without crosslinking of any of the components of the composition.

In certain embodiments, the foam compositions are formed by mixing an aqueous slurry of a cellulosic foam stabilizer with a sweetener, a natural gum, an optional alkali metal salt, and a flavoring agent or an active ingredient or both a flavoring agent and an active ingredient to form a mixture; thereafter introducing air into the mixture through stirring or bubbling to form a foam; and then dividing the foam into a plurality of discrete portions. Optionally, the method can include drying the discrete portions of foam.

In one embodiment, the mixing can include forming an aqueous solution comprising one or more dissolvable components selected from alkali metal salts, flavoring agents, and active ingredients; mixing a solid mixture comprising a sweetener and a natural gum (e.g., a solid particulate composition) into the aqueous solution; and mixing the aqueous slurry of a cellulosic foam stabilizer into the aqueous solution. The addition of the solid composition and the aqueous slurry can occur in any order.

In another embodiment, the mixing can include mixing one or more dissolvable components selected from alkali metal salts, flavoring agents, and active ingredients with the aqueous slurry of a cellulosic foam stabilizer to form a first mixture; and therafter mixing a solid mixture comprising a sweetener and a natural gum (e.g., as a particulate mixture) into the first mixture.

In another embodiment, two separate foams could be formed and then combined into a final product. For example, one foam composition could contain nicotine and an organic acid combined in a salt form, and the other foam composition could contain a buffering agent. Any of the other types of ingredients noted herein could also be included in either foam. Both foam compositions would typically include a cellulosic foam stabilizer, a sweetener, optionally a natural gum, and water. Nicotine in the salt form is more stable and less volatile.

The combination of the two foam compositions could be performed in a number of different ways. For example, one composition could be dried before the other composition is applied and then dried further, or one composition could be applied adjacent to the second one and both dried together. In one embodiment, stripes of one foam composition could be extruded and, after partial drying, stripes of the other foam composition could be extruded between adjacent stripes of the first composition. Alternatively, the two compositions could be extruded simultaneously into alternating stripes and both dried together. Another format could be a tube or ring of one composition filled with the second composition. Still further, flat sheets of the two compositions could be made and dried, then adhered together before cutting into the desired shape. Because of the foamed structure, even if the two compositions touch when wet, only a very small amount of the acid and base would react before drying and the separate compositions would be largely preserved until placed in the mouth for rapid dissolution.

The various components of the composition may be contacted, combined, or mixed together using any mixing technique or equipment known in the art. Any mixing method that brings the mixture ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

Configured for Oral Use

Provided herein is a product configured for oral use. The term "configured for oral use" as used herein means that the product is provided in a form such that during use, one or more of the components of the composition (e.g., flavoring agents and/or nicotine) passes into the mouth of the user. In certain embodiments, the product is adapted to deliver components to a user through mucous membranes in the user's mouth and, in some instances, said component is an active ingredient (including, but not limited to, for example, nicotine) that can be absorbed through the mucous membranes in the mouth when the product is used.

The foam composition of the disclosure is typically used in discrete portions that can be individually placed in the mouth of the user. In certain embodiments, the amount of the foam composition of the disclosure administered per discrete portion is between about 25 mg to about 300 mg, such as about 50 mg to about 200 mg. Where the composition of the invention includes an active ingredient, such as nicotine, in certain embodiments, the amount of active ingredient administered per discrete portion or unit is between about 0.1 mg to about 10 mg, such as about 0.2 to about 7.5 mg, or about 1 to about 5 mg.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXPERIMENTAL

Aspects of the present invention are more fully illustrated by the following examples, which are set forth to illustrate certain aspects of the present invention and are not to be construed as limiting thereof.

Example 1

A slurry of hydroxypropyl methylcellulose was prepared for use in the remaining examples. 11.97 g of BENECEL™ E50 (HPMC) was added to 515 g of boiling water in a blender to give a 2.27% mixture. After blending, the mixture was cooled over an ice bath with intermittent stirring. The mixture was then placed in a refrigerator and stored overnight to hydrate.

Example 2

A composition comprising the ingredients set forth in Table 1 below was prepared.

TABLE 1

| Ingredient | Amount (g) | Amount (% by weight) |
|---|---|---|
| BENECEL ™ E50 aqueous slurry as prepared in Example 1 | 29.7 | 8.26 |
| Water | 275 | 76.46 |
| Xanthan gum | 1.2 | 0.33 |
| Isomalt | 40 | 11.12 |
| Maltodextrin | 10 | 2.78 |
| Sodium chloride | 1.1 | 0.31 |
| Aqueous tobacco extract (spray-dried) | 1.27 | 0.35 |
| Sodium bicarbonate | 1.27 | 0.35 |
| Sodium carbonate | 0.12 | 0.03 |
| Sucralose | 0.01 | 0.003 |

Prior to mixing, the isomalt was ground to a powder in a coffee grinder. The isomalt was then mixed with the maltodextrin. The xanthan gum was mixed with 10 g of the isomalt/maltodextrin mixture. The composition was prepared by first adding sodium chloride, spray-dried tobacco extract, sodium carbonate, sodium bicarbonate, and sucralose to 211 g of the water in a mixing vessel with stirring. The xanthan gum, maltodextrin, and isomalt mixture was added to the mixing vessel and blended with a stick blender. The weighed slurry from Example 1 is added to the mixture with the weighing vessel rinsed with the remainder of the water for a quantitative transfer. The composition was blended with a stick blender. The remainder of the maltodextrin/isomalt mixture was slowly added to the mixing vessel while using a KitchenAid mixer with whisk attachment to blend. The KitchenAid mixer with whisk attachment was then set to high to whip mixture until a foam with soft peaks was formed. A portion of the foamed mixture was piped into a pan lined with parchment paper forming individual semi-conical pieces. The remaining foamed mixture was spread onto a separate pan lined with parchment paper. Both pans were placed in a drying cabinet at 60° C. and 25% relative humidity (RH). After slightly more than 1 hour, the partially dried foamed material felt soft and collapsible and dissolved quickly when placed in the mouth. The pans were kept in the drying cabinet overnight and removed after a total drying time of 19.5 hours forming a lightweight crispy material of the same shape as when put in the oven. 50 of the piped pieces weighed 3.26 g for a mean weight of 65.2 mg.

Example 3

A composition comprising the ingredients set forth in Table 2 below was prepared.

TABLE 2

| Ingredient | Amount (g) | Amount (% by weight) |
|---|---|---|
| BENECEL ™ E50 aqueous slurry as prepared in Example 1 | 152.6 | 61.34 |
| Water | 40 | 16.08 |
| Xanthan gum | 0.9 | 0.36 |
| Isomalt | 40 | 16.08 |
| Maltodextrin | 10 | 4.02 |
| Sodium chloride | 1.5 | 0.60 |
| Aqueous tobacco extract (spray-dried) | 1.5 | 0.60 |
| Sodium bicarbonate | 2.25 | 0.90 |
| Sucralose | 0.01 | 0.004 |

The isomalt was ground in a coffee grinder and mixed with the maltodextrin. The xanthan gum was mixed with 10.2 g of this mixture. The composition was prepared by first adding the slurry from Example 1 to a mixing vessel. Sodium chloride, spray-dried tobacco extract, sodium bicarbonate, and sucralose are added to the mixing vessel with gentle stirring until dissolved. The xanthan gum mixture was added to the mixing vessel and blended with a stick blender. A KitchenAid mixer with whisk attachment set to low was used to blend in the remaining maltodextrin/isomalt mixture into the mixing vessel. The mixer with whisk attachment was then set to high in order to whip the mixture into a foam with soft peaks. Two pans were lined with parchment paper. A portion of the resulting foamed mixture was piped into 93 individual semi-conical pieces in one pan and the remainder was spread onto a separate pan similar to Example 2. The pans were placed in a drying cabinet at 60° C. and 25% relative humidity (RH). The foamed material appeared more stiff than the foamed material of Example 2. After 23 hours the pans were removed from the drying cabinet. The crispy pieces felt much stiffer than the pieces from Example 2. Mean weight of the pieces was 163 mg.

What is claimed is:

1. A foam composition, comprising a cellulosic foam stabilizer, a sweetener, about 10% to about 80% by weight water, a nicotine component and optionally a flavoring agent, and optionally a natural gum, wherein the foam composition is non-crosslinked, wherein the sweetener is present in an amount of about 5% to about 30% by weight and comprises isomalt and maltodextrin.

2. The foam composition of claim 1, wherein the cellulosic foam stabilizer is a cellulose ether.

3. The foam composition of claim 2, wherein the cellulose ether is selected from the group consisting of methylcellulose, hydroxypropylcellulose, hydroxypropylmethylcellulose, hydroxyethyl cellulose, carboxymethylcellulose, and combinations thereof.

4. The foam composition of claim 1, wherein the natural gum is selected from the group consisting of xanthan gum, guar gum, gum arabic, ghatti gum, gum tragacanth, karaya gum, locust bean gum, gellan gum, and combinations thereof.

5. The foam composition of claim 1, further comprising one or more salts.

6. The foam composition of claim 5, wherein the one or more salts are alkali metal salts selected from the group consisting of sodium chloride, sodium carbonate, sodium bicarbonate, and combinations thereof.

7. The foam composition of claim 1, comprising an aqueous tobacco extract.

8. The foam composition of claim 1, comprising from about 0.001 to about 10% by weight of the nicotine component, calculated as the free base and based on the total weight of the composition.

9. The foam composition of claim 1, wherein the composition is substantially free of tobacco material, excluding any nicotine component present.

10. The foam composition of claim 1, comprising:
 about 10 to about 80% by weight water;
 about 5 to about 75% by weight of cellulosic foam stabilizer;
 about 5 to about 30% by weight of sweetener;
 about 0.1 to about 5% by weight of natural gum;
 optionally, about 0.1 to about 5% by weight of one or more alkali metal salts; and
 about 0.001 to about 10% by weight of one or more active ingredients, flavoring agents, or combinations thereof.

* * * * *